(12) United States Patent
Lueers et al.

(10) Patent No.: US 8,205,481 B2
(45) Date of Patent: Jun. 26, 2012

(54) METHOD AND DEVICE FOR MEASURING THE POLLUTANTS IN EXHAUST GASES OF INTERNAL COMBUSTION ENGINES

(75) Inventors: Bernhard Lueers, Aachen (DE);
Juergen Schnitzler, Herzogenrath-Kolscheid (DE); Peter Mauermann, Arnsberg (DE); Peter Gerhards, Stolberg (DE)

(73) Assignee: FEV GmbH, Aachen (DE)

( * ) Notice: Subject to any disclaimer, the term of this patent is extended or adjusted under 35 U.S.C. 154(b) by 744 days.

(21) Appl. No.: 12/302,169

(22) PCT Filed: May 23, 2007

(86) PCT No.: PCT/EP2007/004571
§ 371 (c)(1),
(2), (4) Date: Nov. 24, 2008

(87) PCT Pub. No.: WO2007/134850
PCT Pub. Date: Nov. 29, 2007

(65) Prior Publication Data
US 2009/0139306 A1    Jun. 4, 2009

(30) Foreign Application Priority Data
May 23, 2006 (DE) .......................... 10 2006 024 248

(51) Int. Cl.
*G01N 33/00* (2006.01)
*G01N 1/22* (2006.01)
*G01N 1/26* (2006.01)

(52) U.S. Cl. .................... 73/23.31; 436/118; 73/863.03
(58) Field of Classification Search .................. 436/116, 436/117, 118; 73/23.31, 31.03
See application file for complete search history.

(56) References Cited

U.S. PATENT DOCUMENTS

| 4,829,183 | A | 5/1989 | McClatchie et al. |
| 5,807,750 | A | 9/1998 | Baum et al. |
| 6,151,952 | A * | 11/2000 | Mathews et al. ............. 73/23.31 |
| 2003/0082821 | A1* | 5/2003 | Lanier et al. .................. 436/118 |

FOREIGN PATENT DOCUMENTS

| AT | 403212 A | 12/1997 |
| DE | 2836787 A1 | 3/1980 |
| DE | 3339073 A1 | 5/1985 |
| DE | 19527557 B4 | 2/1996 |
| DE | 10202859 A1 | 8/2003 |

* cited by examiner

*Primary Examiner* — Harshad Patel
*Assistant Examiner* — Punam Roy
(74) *Attorney, Agent, or Firm* — Gifford, Krass, Sprinkle, Anderson & Citkowski, P.C.

(57) ABSTRACT

A method of measuring oxygen-containing nitrogen components including nitrogen dioxide in exhaust gases of internal combustion engines, wherein an exhaust gas sample is taken from a removal point 10 at the exhaust gas pipe 1 and is guided to at least one measuring instrument by means of a removal line, wherein, for the purpose of measuring the oxygen-containing nitrogen components, there are provided a separate removal point 10 and a removal line 11 and that the exhaust gas sample for measuring the oxygen-containing nitrogen components is set to a temperature at which a reaction between the nitrogen dioxide and soot is low.

21 Claims, 3 Drawing Sheets

METHOD AND DEVICE FOR MEASURING THE POLLUTANTS IN EXHAUST GASES OF INTERNAL COMBUSTION ENGINES

CROSS-REFERENCE TO RELATED APPLICATIONS

This application is the U.S. national phase of PCT/EP2007/004571 filed May 23, 2007, which claims priority of German patent application 10 2006 024 248.3 filed May 23, 2006.

FIELD OF THE INVENTION

The invention relates to a method of measuring oxygen-containing nitrogen components including nitrogen dioxides in exhaust gases of internal combustion engines, wherein an exhaust gas sample is taken from a removal point at the exhaust gas pipe and is guided to at least one measuring device by means of a removal line; the invention also relates to a device for measuring oxygen-containing nitrogen components including nitrogen dioxide in exhaust gases of internal combustion engines, wherein a removal line is branched off a removal point for an exhaust gas sample at the exhaust gas pipe and guided to at least one measuring device.

BACKGROUND OF THE INVENTION

More particularly when developing and operating internal combustion engines operated by lean fuels, it becomes more and more important to continuously determine acid, oxygen-containing nitrogen components such as nitrogen dioxide $NO_2$. In addition to a more stringent exhaust gas legislation which leads to a maximum permissible emission limit for $NO_2$, an accurate determination of nitrogen oxide fractions in the exhaust gas plays an important part for the subsequent treatment of exhaust gases.

It is generally known to provide a removal point in the exhaust gas pipe and a removal line for simultaneously measuring all exhaust gases, more particularly nitrogen oxide $NO_x$ and hydrocarbons HC.

From DE 33 39 073 A1 there are known a method and a device for analyzing gas mixtures, wherein individual partial gas flows are guided to individual analyzing devices, for example for nitrogen oxides $NO_x$. The main gas flow is heated in front of a removal point for an exhaust gas sample for measuring hydrocarbons, thereafter guided to a cooler and filter, and of said main gas flow conditioned in said way, there are branched off the further partial gas flows for exhaust gas samples for measuring other constituents such as nitrogen oxides $NO_x$.

At temperatures of approximately 190° C. which are necessary in order to avoid condensation of hydrocarbons, it is possible for there to occur a partial reduction of the nitrogen dioxide to be measured. Furthermore, there may occur a reaction at surfaces coming into contact with nitrogen dioxide, such as the removal line, bolted connections and the like. Above all, a surface reaction has been observed on steel surfaces, more particularly high-grade steel surfaces.

SUMMARY OF THE INVENTION

It is therefore the object of the invention to avoid the above-described disadvantages and prevent or reduce a catalytic reduction of the nitrogen dioxide at the surfaces of the removal line and a reduction of nitrogen dioxide and a reaction of nitrogen dioxide with soot.

The objective is achieved by providing a method of measuring oxygen-containing nitrogen components including nitrogen dioxides in exhaust gases of internal combustion engines, wherein an exhaust gas sample is taken from a removal point at the exhaust gas pipe and is guided to at least one measuring instrument by means of a removal line, and wherein, for the purpose of measuring the oxygen-containing nitrogen components, there are provided a separate removal point and removal line and that the exhaust gas sample for measuring the oxygen-containing nitrogen components is set to a temperature at which the possibility of there occurring a reaction between the nitrogen dioxide and soot is slight. More particularly, it is proposed that the exhaust gas sample for measuring the oxygen-containing nitrogen components is guided to the measuring device by surfaces which are passivated or passive relative to a reaction with nitrogen dioxide with soot. According to a preferred embodiment, the exhaust gas sample for measuring the oxygen-containing nitrogen components is guided to the measuring device via a pre-filter, more particularly a soot pre-filter. In this context, it is proposed that the temperature of the exhaust gas sample for measuring the oxygen-containing nitrogen components are tempered to a reduced level in the removal line and/or at a filter holding device of a pre-filter. Said temperature should be lowered to a level which is lower than that of an exhaust gas sample for measuring hydrocarbons, which sample can be guided via a separate removing point and removal line.

The desired result is achieved more particularly if the exhaust gas sample for measuring the oxygen-containing nitrogen components is tempered to or below 170° C., preferably to or below 120° C. According to a preferred embodiment, the exhaust gas sample for measuring the oxygen-containing nitrogen components is held at 5° C., preferably at 20° C. above the dew point temperature of the water fraction in the exhaust gas sample. The tempering process can be carried out by a thermostatically controlled electric device or a device operated by a thermal transfer medium, preferably at the outer circumference of the removal line and/or of a filter holding device and/or of a casing of a pre-filter. Care has to be taken to ensure that the soot covering and/or soot layer in the pre-filter is limited to 25 μm. If this value is exceeded the pre-filter insert has to be cleaned or replaced. Such a measure reduces the risk of a reduction taking place.

An inventive device for measuring oxygen-containing nitrogen components including nitrogen dioxide in exhaust gases of internal combustion engines, wherein a removal line is branched off a removal point for an exhaust gas sample at the exhaust gas pipe and guided to at least one measuring device is characterized in that for the purpose of measuring the oxygen-containing nitrogen components, there are provided a separate removal point and removal line and that the removal line is set to a temperature at which the possibility of there occurring a reaction between the nitrogen dioxide and soot is only slight. It is proposed that the surfaces coming into contact with the exhaust gas sample for measuring the oxygen-containing nitrogen components are passivated or are passive relative to a reaction with nitrogen dioxide. The removal line for measuring the oxygen-containing nitrogen components should comprise a built-in pre-filter, more particularly a soot pre-filter. The removal line and/or a filter holding device of a pre-filter incorporated into said removal line are/is preferably set to a temperature level which is below the exhaust gas temperature. The temperature level should be below that of a separate removal line for an exhaust gas sample for measuring the hydrocarbons. More particularly, the temperature of the wall surfaces of the removal line for measuring oxygen-containing nitrogen components and/or of a filter holding device and/or other components in the exhaust gas line leading to the measuring instruments for the nitrogen components is 170° C. or lower preferably 120° C. or lower. The temperature of the wall surfaces is set to such a temperature that the exhaust gas sample for measuring the oxygen-containing nitrogen components is held at least 5° C., but preferably 20° C. above the dew point temperature of a water fraction in the exhaust gas sample.

The surfaces coming into contact with the exhaust gas sample, surfaces such as the removal line and/or connecting elements, fittings, filter holding devices and/or casings should consist of steel or high-grade steel which, alternately, has been subjected to a threefold to five-fold alternating nitriding and phosphating process. Alternatively, it is also possible to use titanium as the material for said components. The pre-filter for the measuring instruments for the oxygen components can be provided in the form of a surface filter.

The invention thus relates to a measuring method for accurately determining more particularly the nitrogen dioxide concentration in exhaust gas, in the foreground of the invention being the reduction of the reactivity of hot exhaust gases with the surrounding materials such as the removal line, bolted connection, fittings etc. This also applies to a pre-filter optionally built into the removal line, especially a soot filter. In this way, it is possible to avoid pre-reactions and the unfalsified NO, content in the exhaust gas sample is guided as far as the measuring instrument. In principle, this is achieved by two measures:

separating the removal lines and optionally the removal points for the exhaust gas samples for measuring nitrogen oxide, more particularly nitrogen dioxide and hydrocarbon, and lowering the temperature of the exhaust gas sample and of the wall temperature relative to conventional methods which only use one removal line.

Further embodiments of the invention are referred to in the following description of the drawings and in the sub-claims.

BRIEF DESCRIPTION OF THE DRAWINGS

Below, the invention will be explained with reference to the embodiments illustrated in the enclosed figures wherein.

DETAILED DESCRIPTION OF THE PREFERRED EMBODIMENTS

Figure 1:
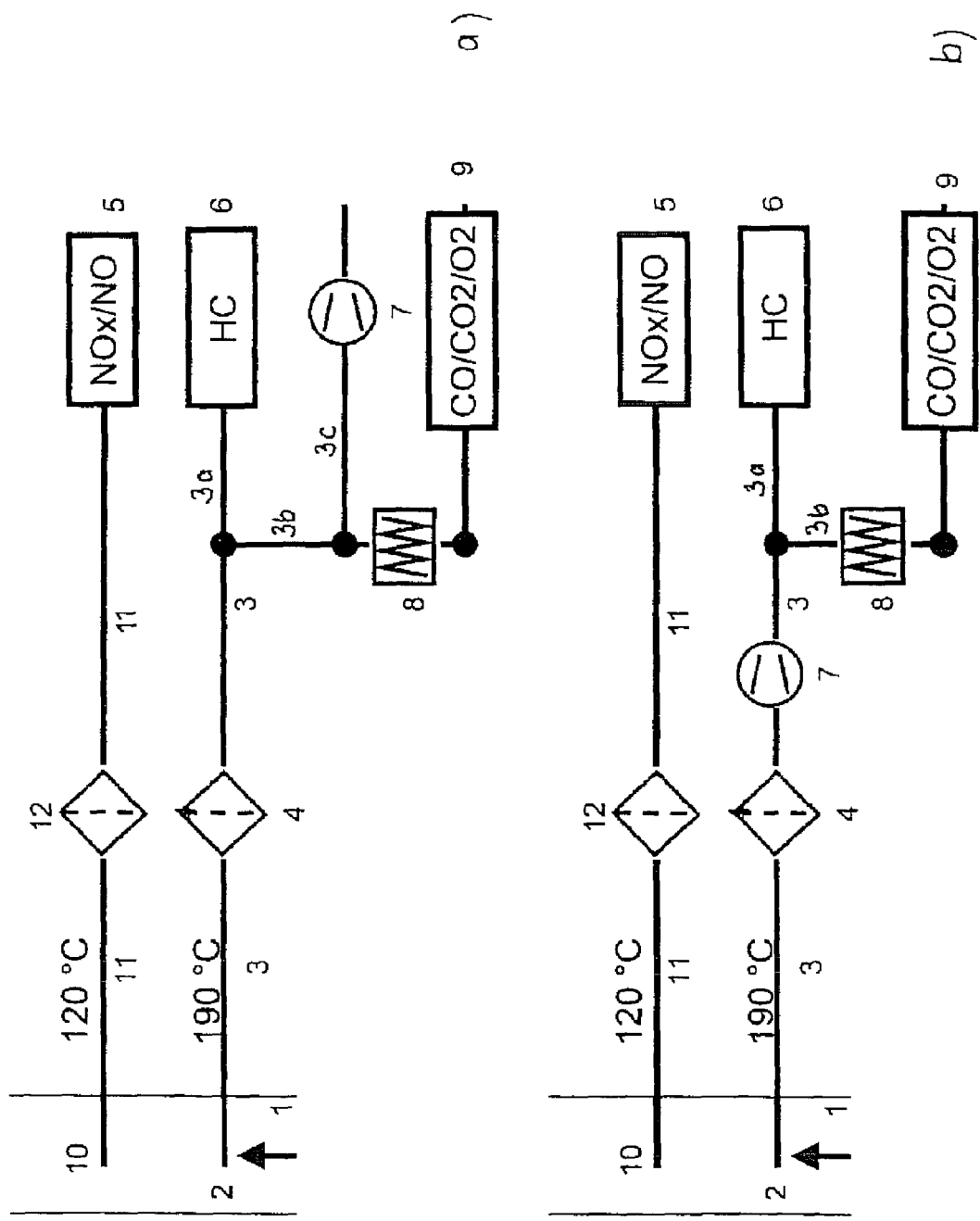
FIG. 1 shows a diagram of a device for measuring the nitrogen components in the exhaust gas of an internal combustion engine
 a) in a first embodiment
 b) in a second embodiment.

In FIGS. 1 to 4, to the extent they show details, there is illustrated an exhaust gas pipe 1 of an internal combustion engine. The two illustrations of FIG. 1 will initially be described jointly below. An exhaust gas pipe 1 is provided with a first removal point 2 winch changes into the removal line 3. The removal line 3 is heated to 190° C. and comprises a pre-filter 4 for separating the particle emissions. The removal line 3 is of the branched type and, via a branch 3a, leads to a measuring instrument 6 for determining hydrocarbons, such as an FID (flame ionization detector) or an FTIR (Fourier transformation infrared absorption analyzer). The second branch 3b leads via a cooler 8 to the measuring instruments 9 for determining the CO, $CO_2$ and $O_2$ concentrations.

In the exhaust gas pipe 1, behind the first removal point 2, there is provided a second removal point 10 which changes into a sample removing line 11 which consists of passivated high-grade steel or the like or of a passive material such as titanium and is preheated to a maximum temperature of 120° C. In the sample removing line 11, there is provided a pre-filter 12 which can also be heated to a maximum temperature of 120° C. and which, like the line 11, consists of a passivated material or of a passive material. This pre-filter, too, serves to separate the particle emissions. Behind the pre-filter 12, there is provided a measuring instrument for determining the oxygen-containing nitrogen components, more particularly the nitrogen oxide components $NO_x$ and NO, such as a CLD (chemical-luminescence detector) or an FTIR (Fourier transformation infrared absorption analyzer).

In illustration a), a line 3c branches off from line 3b and comprises a pump 7 in the form of a bypass pump, whereas in illustration b) a line 3 in the form of a pressure pump is arranged on the lines 3a and 3b in front of the branching point. To the extent that the measuring instruments 6, 9, which are provided with their own pumps, comprise an adequate pump capacity, there is no need for an external pump capacity.

Figure 3:
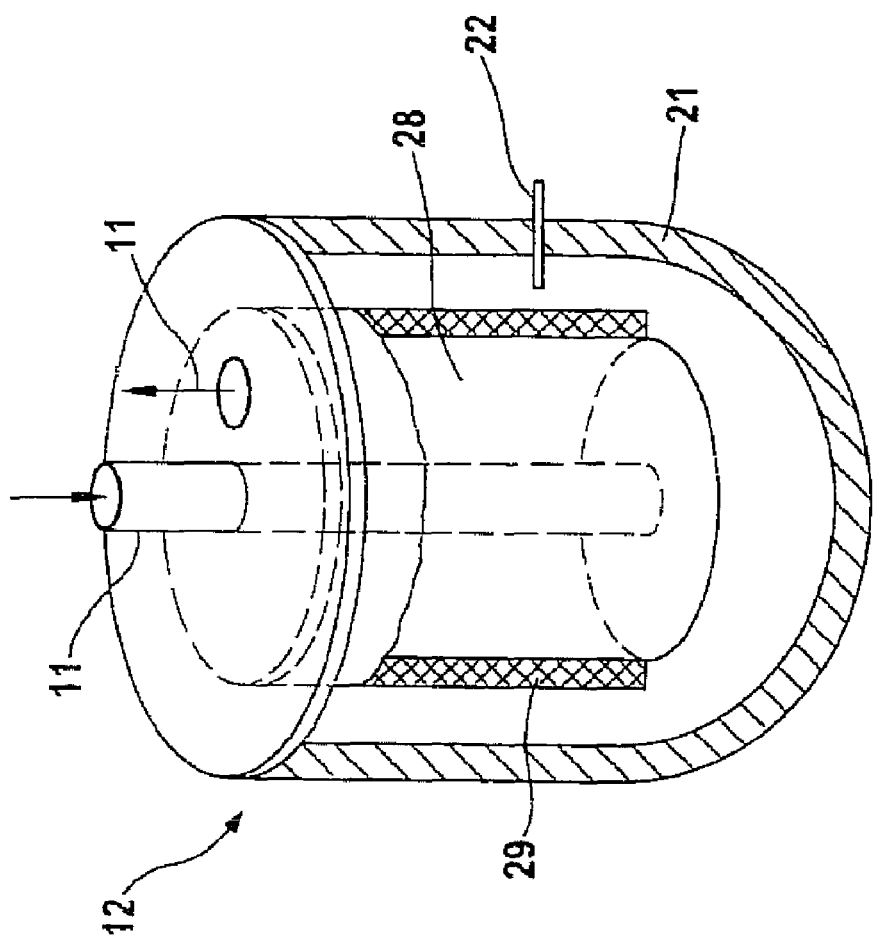
FIG. 3 shows a pre-filter according to FIG. 2 in a modified embodiment.

In the embodiment according to FIG. 3, the pre-filter 12 is dish-shaped. It comprises a cylindrical filter holding device 28 with a cylindrical soot filter 29 which is enclosed by a casing 21 on whose outer circumference there is arranged the device 20. For monitoring the temperature, a thermo-element 22 is located between the soot filter 29 and the casing 21.

Figure 2:
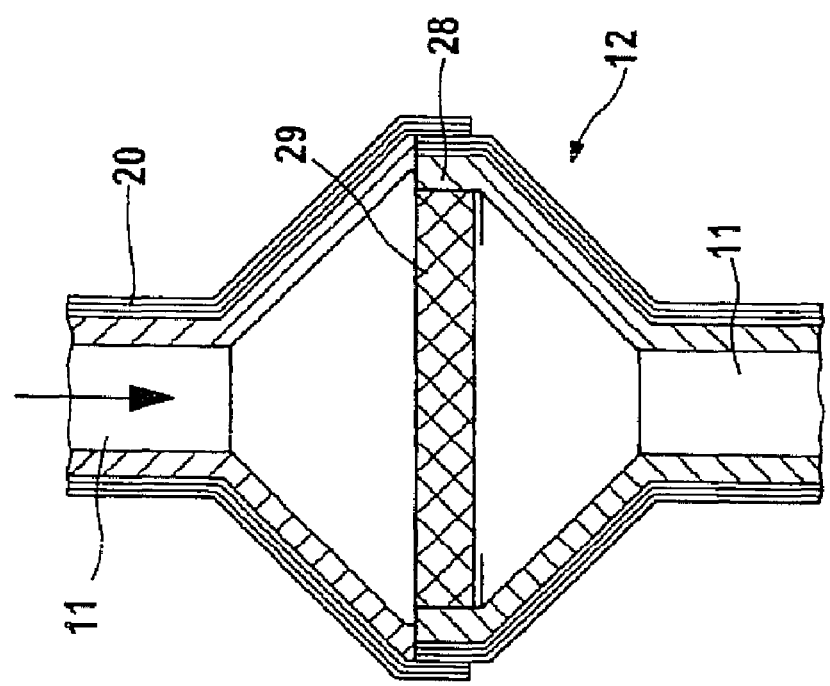
FIG. 2 shows a pre-filter incorporated into the device.
Figure 4:
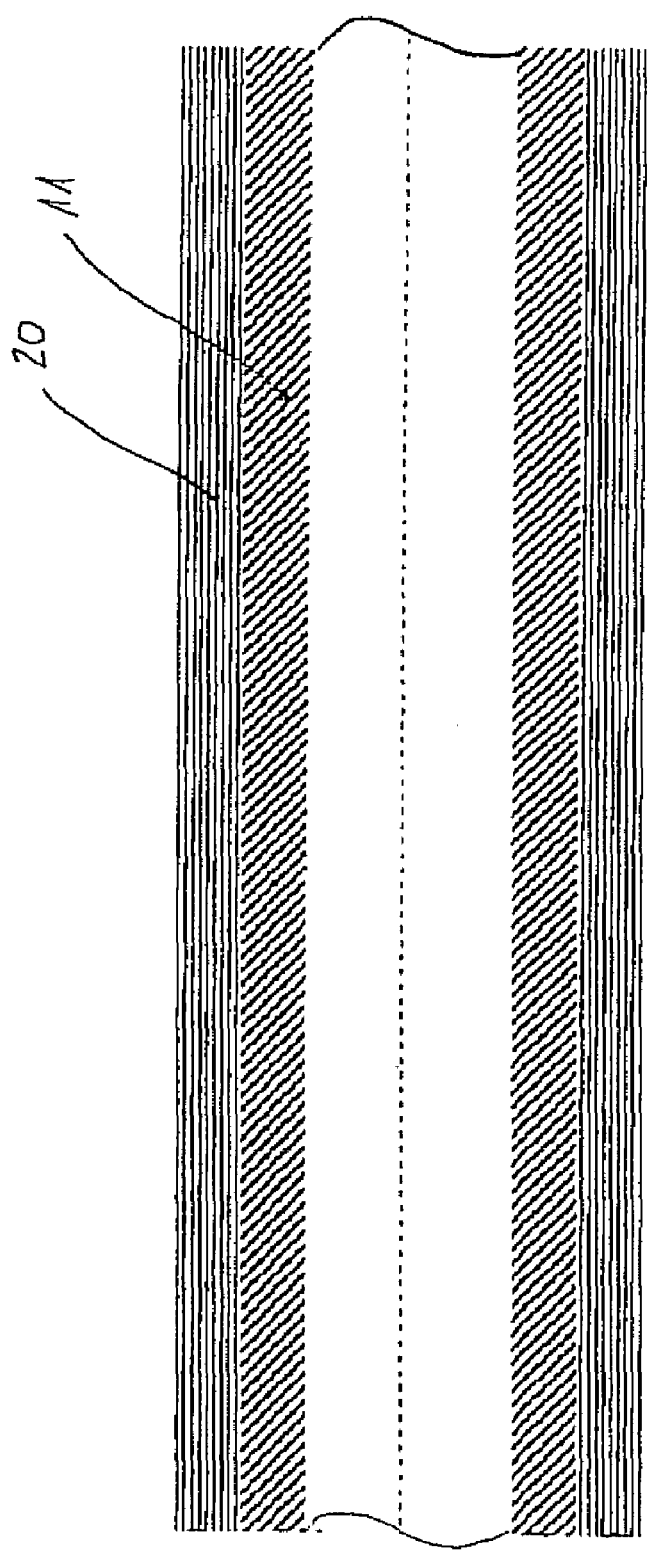
FIG. 4 shows part of a removal line for the exhaust gas sample.

The piece of pipe according to FIG. 4 comprises the removal line 11 and the device 20 for lowering the temperature, which device 20 is designed in accordance with the device for heating and cooling purposes as described in connection with FIG. 2. All the surfaces of the removal line of the filter holding device which are contacted by the exhaust gas sample can either be passivated as defined in the patent claims or they can be produced entirely from titanium in order to avoid a reaction of the nitrogen dioxide. Furthermore, a reaction with soot in the pre-filter is reduced in that the amount of soot such as the covering of the filter, more particularly, the soot layer, is reduced to 25 μm.

The invention claimed is:

1. A method of measuring at least two exhaust gas components in exhaust gases of internal combustion engines, the method comprising the steps of:
  taking a first exhaust gas sample from a first removal point at the exhaust gas pipe;
  delivering the first exhaust gas sample by means of a first removal line to at least one first measuring instrument for measuring a first gas component from the first exhaust gas sample;
  taking a second exhaust gas sample from the first removal point or from a second removal point at the exhaust gas pipe;
  setting the temperature of the second exhaust gas sample for measuring the oxygen-containing nitrogen compound to a temperature which is different than a temperature of the first exhaust gas sample; and
  delivering the second gas exhaust sample by means of a second removal line to at least one second measuring instrument for measuring an oxygen-containing nitrogen exhaust-gas component, wherein the second removal line is separate from the first removal line.

2. A method according to claim 1,
  including the step of guiding the second exhaust gas sample for measuring the oxygen-containing nitrogen component to the at least one second measuring device by surfaces which are passivated or passive relative to a reaction with nitrogen dioxide.

3. A method according to claim 1,
including the step of guiding the second exhaust gas sample for measuring the oxygen-containing nitrogen component to the at least one second measuring device via a soot pre-filter.

4. A method according to claim 1,
including the step of lowering the temperature of the second exhaust gas sample for measuring the oxygen-containing nitrogen component to a level less than 190° C.

5. A method according to claim 1, wherein the first exhaust gas sample is taken from the first removal point which is separate from the second removal point from which the second exhaust gas sample is taken.

6. A method according to claim 1,
including the step of lowering the temperature of the second exhaust gas sample for measuring the oxygen-containing nitrogen component to a reduced level in the second removal line and/or at a filter holding device of a pre-filter.

7. A method according to claim 6,
wherein the lowering the temperature of the second exhaust gas sample is carried out by a thermostatically controlled electric device or a device operated by a thermal transfer medium.

8. A method according to claim 1,
including the step of lowering the temperature of the second exhaust gas sample for measuring the oxygen-containing nitrogen component to or below 170° C.

9. A method according to claim 8,
including the step of holding the second exhaust gas sample for measuring the oxygen-containing nitrogen component to at least 5° C. above the dew point temperature of the water fraction in the exhaust gas sample.

10. A device for measuring oxygen-containing nitrogen components in exhaust gases of internal combustion engines comprising:
a first removal line leading from a first removal point at an exhaust pipe and for a first exhaust gas sample guided to at least one first measuring device for measuring a first exhaust gas component,
a second removal line which is separate from said first removal line and leads from said first removal point or a second removal point at said exhaust gas pipe and for a second exhaust gas sample guided to at least one second measuring device for measuring an oxygen-containing nitrogen component,
wherein said second removal line is set to a temperature which is different than a temperature of said first removal line.

11. A device according to claim 10,
wherein surfaces coming into contact with said second exhaust gas sample for measuring the oxygen-containing nitrogen component are passivated or are passive relative to a reaction with nitrogen dioxide.

12. A device according to claim 10,
wherein said second removal line for measuring said oxygen-containing nitrogen component and/or a filter holding device of a pre-filter incorporated into said second removal line are set to a temperature level which is below an exhaust gas temperature.

13. A device according to claim 10,
wherein said second removal line for measuring said oxygen-containing nitrogen component and/or a filter holding device of a pre-filter incorporated into said second removal line are set to a temperature level which is lower than that of said first removal line.

14. A device according to claim 10,
further comprising a thermostatically controlled electric device or a device operated by a thermal transfer medium for setting said temperature for said second removal line.

15. A device according to claim 10,
wherein surfaces coming into contact with said second exhaust gas sample for measuring said oxygen-containing nitrogen component consist of steel or high-grade steel which has been subjected to a threefold to five-fold alternating nitriding and phosphating process.

16. A device according to claim 10,
further comprising a titanium surface for said second exhaust gas sample to come into contact therewith.

17. A device according to claim 10, wherein said first removal line is leading from said first removal point to the at least one first measuring device and said second removal line is leading from said second removal point to the at least one second measuring device.

18. A device according to claim 10,
wherein said second removal line for measuring said oxygen-containing nitrogen component comprises a built-in pre-filter.

19. A device according to claim 18 wherein said pre-filter has a soot coating and/or a soot layer with a thickness equal to or less than 25 μm.

20. A device according to claim 10,
wherein a temperature of wall surfaces of said second removal line for measuring said oxygen-containing nitrogen component and/or of a filter holding device is equal to or less than 170° C.

21. A device according to claim 20,
wherein said temperature of said wall surfaces is at least 5° C. above a dew point temperature of a water fraction in said second exhaust gas sample for measuring said oxygen-containing nitrogen-component.

* * * * *

UNITED STATES PATENT AND TRADEMARK OFFICE
CERTIFICATE OF CORRECTION

| | | |
|---|---|---|
| PATENT NO. | : 8,205,481 B2 | Page 1 of 1 |
| APPLICATION NO. | : 12/302169 | |
| DATED | : June 26, 2012 | |
| INVENTOR(S) | : Bernhard Lüers et al. | |

It is certified that error appears in the above-identified patent and that said Letters Patent is hereby corrected as shown below:

In the Specification:

At Column 3, Line Number 26, delete "NO,", insert --$NO_2$--

Signed and Sealed this
Twenty-fifth Day of December, 2012

David J. Kappos
*Director of the United States Patent and Trademark Office*